United States Patent [19]

Polito

[11] 4,116,773

[45] Sep. 26, 1978

[54] ENZYMATIC REAGENT AND METHOD FOR INCREASING THE SENSITIVITY OF ENZYMATIC SUBSTRATE ANALYSES USING OXYGEN RATE ANALYZERS

[75] Inventor: Carole A. Polito, Costa Mesa, Calif.

[73] Assignee: Beckman Instruments, Inc., Fullerton, Calif.

[21] Appl. No.: 701,920

[22] Filed: Jul. 1, 1976

[51] Int. Cl.$^2$ ............... G01N 33/00; G01N 31/14
[52] U.S. Cl. ........................ 195/99; 195/103.5 R; 195/103.5 C
[58] Field of Search ............... 195/103.5 R, 103.5 C, 195/99

[56] References Cited
U.S. PATENT DOCUMENTS 3,857,771   12/1974   Sternberg ............... 195/103.5 R Primary Examiner—Alvin E. Tanenholtz
Assistant Examiner—C. A. Fan
Attorney, Agent, or Firm—R. J. Steinmeyer; R. R. Meads; R. S. Frieman

[57] ABSTRACT

A novel enzymatic reagent and method is provided for increasing the sensitivity of enzymatic substrate analyses using oxygen rate analyzers. The reagent is a buffered solution containing an enzyme which reacts specifically with oxygen and with the substrate being measured. The reagent also contains a salt or a combination of salts in quantities sufficient to reduce the solubility of oxygen in the reagent by at least thirty percent when compared to the solubility of oxygen in water. Upon being mixed with a specimen containing the specific enzyme substrate being measured, the enzyme catalyzes the reaction of the substrate and the oxygen. The rate of reaction of oxygen is measured, and the amount of total substrate is determined by means which translate the rate of oxygen consumption into the concentration of total substrate present in the specimen.

9 Claims, No Drawings

ENZYMATIC REAGENT AND METHOD FOR INCREASING THE SENSITIVITY OF ENZYMATIC SUBSTRATE ANALYSES USING OXYGEN RATE ANALYZERS

BACKGROUND OF THE INVENTION

A particularly useful method and apparatus for measuring the concentration of enzymatic substrates in sample solutions is described in U.S. Pat. Nos. 3,857,771 and 3,933,593 to James C. Sternberg. In particular, the Sternberg patents describe analyzers and methods for determining initial enzymatic substrate concentrations by measuring the rate at which oxygen is consumed in a chemical reaction including the enzymatic substrate.

While the Sternberg and other similar oxygen rate analyzers provide means for rapidly determining initial enzymatic substrate concentrations, the signals generated in such analyzers and indicative of such concentrations sometimes are quite small. Under such circumstances, it is desired to substantially raise the oxygen rate analyzer's sensitivity, referred to as the signal-to-noise ratio.

SUMMARY OF THE INVENTION

It has been discovered that if a salt or combination of salts is included in enzyme reagents which react with oxygen in samples containing enzyme substrates to be measured, the solubility of oxygen in the reagent is reduced. More particularly, it has been discovered that the inclusion of such salts in quantities sufficient to reduce the solubility of oxygen in the reagent by at least 30% when compared to the solubility of oxygen in water, results in a significant and unexpected improvement in the signal-to-noise ratio (sensitivity) of signals generated in oxygen rate analyzers and indicative of initial enzyme substrate concentrations. These discoveries appear to be based upon the observation that as the solubility of oxygen in an enzymatic reagent decreases, less oxygen is available to rect with the enzymatic reagent. In oxygen ratio analyzers that employ polarographic sensors and compute initial enzymatic substrate concentrations based upon a rate of change of oxygen consumption, this means that the same rate of change in oxygen concentration will be sensed as a greater rate of change of oxygen consumption than before. When polarographic oxygen sensors are used, the partial pressure rather than the dissolved concentration of oxygen is measured. In a given medium, the partial pressure is proportional to the concentration. If the oxygen solubility is reduced, the proportionately constant becomes greater, and a greater partial pressure change, and hence a greater decrease in sensor output, results from the same oxygen concentration decrease. This produces a proportionately greater signal and results in a substantial improvement in the resulting signal-to-noise ratio associated with the analyzer without any alteration of its associated electronics.

For example, it has been found that when a phosphate salt of about 1.0 molar solution is included in an enzymatic reagent used in the aforesaid Sternberg type of oxygen rate analyzer to measure cholesterol concentration, the solubility of oxygen in the reagent is decreased by more than 30% and the resulting signal indicative of initial cholesterol concentration is increased tenfold when compared to the signal output in the absence of the phosphate salt.

DESCRIPTION OF PREFERRED EMBODIMENTS OF THE INVENTION

Embodiments of the invention provided for herein are described in terms of specific reagent systems for specific substrate assays. It is to be understood, however, that the invention is not limited thereto but comprehends any enzymatic reagent system which may be used with an oxygen rate analyzer to measure substrate concentrations.

Cholesterol Assay

In the context of a reagent for the assay of cholesterol, the salts found to satisfactorily reduce oxygen solubility were selected from the group comprising a mixture of potassium dihydrogenphosphate and sodium monohydrogenphosphate in any ratio, ammonium sulfate, sodium sulfate and potassium chloride.

In determining the optimum reduction in solubility of oxygen in the reagent to be at least 30% when compared to the solubility of oxygen in water, it was found that concentrations of the salts producing such solubility reductions will vary with the particular formulations of the reference reagents. Bearing in mind the optimum solubility reduction of at least 30% for oxygen, such concentrations may be readily determined by one skilled in the art having the benefit of the invention disclosed herein.

For the purpose of illustrating the invention, however, specific salt concentrations and their resultant effect upon oxygen solubility in a reference reagent formulation and the corresponding signal increase in a Sternberg-type oxygen rate analyzer are set forth in Table I. The reference reagent formulation used for the cholesterol assay was an aqueous solution comprising 0.01 M solution of potassium phosphate having a pH of 6.0, 0.5 milligrams per milliliter of sodium cholate, 0.02 grams of Triton X-100 (a brand name for the surfactant iso-octylphenoxypolyethoxyethanol containing approximately ten molecules of ethylene oxide per molecule of polymer per 100 ml of solution), 0.001 M solution of sodium azide, one International Unit of Cholesterol Oxidase (*Brevibacterium* sp.), E.C.1.1.3.6 and 0.02 International Units of Cholesterol Esterase E.C.3.1.1.13.

Table I

| Salt | Molarity of Reagent Solution | Percent Decrease in Oxygen Content | Increase of Magnitude of Signal |
|---|---|---|---|
| $KH_2PO_4$ and $Na_2HPO_4$ | 1.0* | 60 | 10 fold |
| $KH_2PO_4$ and $Na_2HPO_4$ | 0.50* | 40 | 4 fold |
| $(NH_4)_2SO_4$ | 0.75 | 35 | 10 fold |
| $Na_2SO_4$ | 0.50 | 35 | 7 fold |
| KCl | 1.50 | 35 | 4 fold |

*The molarity of the reagent solution includes the molarity contributed by potassium phosphate in the reference reagent formulation.
**The increase is compared against the signal produced by the use of identical reagents but without the presence of any one of the salts set forth in the Table.

Glucose Assay

In the context of a reagent for a glucose assay, the salts found to satisfactorily reduce the oxygen solubility were selected from the group comprising a mixture of potassium dihydrogenphosphate and sodium monohydrogenphosphate, ammonium sulfate, and sodium sulfate. As with the cholesterol assay, the concentrations of said salts producing the optimum reduction in oxygen solubility of at least 30% were found to vary with the formulations of the reference reagents. Again, with the benefit of the invention disclosed herein, such concentrations may be readily determined by one skilled in the art.

For the purpose of illustrating the invention, however, specific salt concentrations and the resultant effect upon oxygen solubility in a reference reagent formulation and the corresponding signal increase in the oxygen rate analyzer are set forth in Table II. The reference reagent formulation used for the glucose assay was an aqueous solution comprising 0.2 M solution of sodium phosphate having a pH of 6.0, 0.01 M solution of potassium iodide, 0.0075 M solution of ammonium molybdate, 0.0005 M solution of iodine, 5% by weight of ethanol, and 150 International Units per milliliter of glucose oxidase.

Table II

| Salt | Molarity in Reagent Solution | Percent Decrease in Oxygen Content | Increase of Magnitude of Signal** |
|---|---|---|---|
| $KH_2PO_4$ and $Na_2HPO_4$ | 1.5* | 65 | 25 |
| $(NH_4)_2SO_4$ | 1.5 | 50 | 35 |
| $Na_2SO_4$ | 1.25 | 60 | 53 |

*The molarity of the reagent solution includes the molarity contributed by potassium phosphate in the reference reagent formulation.
**The increase is compared against the signal produced by the use of identical reagents but without the presence of any one of the salts set forth in the Table.

Uric Acid Assay

In the context of a reagent for the assay of uric acid, a salt which was found to satisfactorily reduce oxygen solubility is sodium monohydrogenphosphate. The concentration thereof will vary depending upon the particular formulation of the reagent and may be determined empirically be one skilled in the art having the benefit of the invention disclosed herein. For the purpose of illustrating the invention, however, it was found that addition of sodium monohydrogenphosphate in an amount to produce a molarity of 0.75 resulted in a 45% decrease in the oxygen content of the reagent and a 40% increase in the magnitude of the signal of the oxgyen rate analyzer as compared against an identical reagent but without the presence of sodium monohydrogenphosphate. The specific reagent for a uric acid assay used with sodium monohydrogenphosphate is an aqueous solution comprising 0.1 M solution of sodium tetraborate having a pH of 8.5, and 0.25 International Units per milliliter of uricase.

The addition of either ammonium sulfate salt or potassium chloride salt to the aforesaid reagent for the uric acid assay was found to produce a decrease in the oxygen content of the reagent but a decrease in the analyzer signal rather than an increase. It is believed that this decrease in signal was probably caused by inhibition of the uricase by the concentration of the ammonium sulfate or potassium chloride.

Each of the salts contemplated for use in the instant invention will affect every enzyme in a manner specific to that enzyme. As a result, the effect of the salt on the oxygen level and signal response may be partially masked by the effect of the salt on the enzyme itself. For example, the addition of 0.5 M solution of the phosphate salt in Table I relating to the cholesterol reagent, decreases the oxygen content of the reagent by 40% and results in a fourfold increase in signal. However, the addition of 0.5 M solution of sodium sulfate to the same reagent decreases the oxygen content by 35% yet provides for a sevenfold increase in signal. This phenomenon is believed to be due to the fact that the increased level of phosphate ion is inhibiting the rate of reaction of one or both of the enzymes involved in the cholesterol assay, or that the increased level of sodium sulfate is enhancing the rate of reaction of one or both of the enzymes.

Because of the magnitude of the number of salts available for evaluation for use in the present invention, the present invention is not to be construed as limited to particular salts set forth herein, but comprehends the use of all salts or any other compatible agent which may be found by routine testing by a person skilled in the art to significantly decrease the oxygen content of the particular enzymatic reagent to which it is added, and increase the magnitude of the signal of the oxygen rate analyzer with which it is used. Furthermore, while particular embodiments of the invention chosen herein for purposes of disclosure are at present considered to be preferred, it is to be understood that the invention is intended to cover all changes and modifications in the disclosed embodiments which fall within the spirit and scope of the invention.

I claim:

1. An enzymatic reagent comprising a buffered solution and an enzyme for use in the kinetic measurement of the concentration of a substrate by means of an oxygen rate analyzer, characterized in that said reagent further comprises a salt or a mixture of salts which will reduce the solubility of oxygen in said reagent by at least 30% when compared with the solubility of oxygen in water and thereby increase the magnitude of an output signal generated by the analyzer and indicative of said substrate concentration.

2. An enzymatic reagent as set forth in claim 1 for use in the kinetic measurement of the concentration of cholestrol wherein said enzyme is cholesterol oxidase, and said salt or mixture of salts is selected from the group consisting of:
   a. a mixture of potassium dihydrogenphosphate and sodium monohydrogenphosphate,
   b. ammonium sulfate,
   c. sodium sulfate, and
   d. sodium chloride.

3. An enzymatic reagent as set forth in claim 1 for use in the kinetic measurement of the concentration of glucose wherein said enzyme is glucose oxidase, and said salt or mixture of salts is selected from the group consisting of:
   a. a mixture of potassium dihydrogenphosphate and sodium monohydrogenphosphate,
   b. ammonium sulfate, and
   c. sodium sulfate.

4. An enzymatic reagent as set forth in claim 1 for use in the kinetic measurement of the concentration of uric acid wherein said enzyme is uricase, and said salt is sodium monohydrogenphosphate.

5. In an enzymatic method for kinetically measuring substrate concentrations by means of an oxygen rate analyzer using an enzymatic reagent comprising a buffered solution and an enzyme, the improvement consisting of the addition to said reagent of an agent which will reduce the solubility of oxygen in said reagent by at least 30% when compared to the solubility of oxygen in water to thereby increase the magnitude of an output signal generated by the analyzer and indicative of said substrate concentration.

6. In an enzymatic method as set forth in claim 5 wherein said agent is a salt or a mixture of salts.

7. In an enzymatic method as set forth in claim 5 for kinetically measuring the concentration of cholesterol using a cholesterol oxidase containing reagent wherein said agent is selected from the group of salts consisting of:
   a. a mixture of potassium dihydrogenphosphate and sodium monohydrogenphosphate,
   b. ammonium sulfate,
   c. sodium sulfate, and
   d. sodium chloride.

8. In an enzymatic method as set forth in claim 5 for kinetically measuring the concentration of glucose using a glucose oxidase containing reagent wherein said agent is selected from the group of salts consisting of:
   a. a mixture of potassium dihydrogenphosphate and sodium monohydrogenphosphate,
   b. ammonium sulfate, and
   c. sodium sulfate.

9. In an enzymatic method as set forth in claim 5 for kinetically measuring the concentration of uric acid using a uricase containing reagent wherein said agent is sodium monohydrogenphosphate.

* * * * *